(12) United States Patent
Snyder

(10) Patent No.: US 12,029,568 B2
(45) Date of Patent: Jul. 9, 2024

(54) SEPARATE PRINTED TRACES FOR ECG AND DEFIBRILLATION CIRCUITS

(71) Applicant: Conmed Corporation, Utica, NY (US)

(72) Inventor: Jessica Snyder, Poland, NY (US)

(73) Assignee: Conmed Corporation, Utica, NY (US)

( * ) Notice: Subject to any disclaimer, the term of this patent is extended or adjusted under 35 U.S.C. 154(b) by 60 days.

(21) Appl. No.: 17/271,307

(22) PCT Filed: Aug. 28, 2019

(86) PCT No.: PCT/US2019/048452
§ 371 (c)(1),
(2) Date: Feb. 25, 2021

(87) PCT Pub. No.: WO2020/047022
PCT Pub. Date: Mar. 5, 2020

(65) Prior Publication Data
US 2021/0196181 A1    Jul. 1, 2021

Related U.S. Application Data

(60) Provisional application No. 62/725,311, filed on Aug. 31, 2018.

(51) Int. Cl.
*A61B 5/00*   (2006.01)
*A61B 5/263*  (2021.01)
(Continued)

(52) U.S. Cl.
CPC .............. *A61B 5/33* (2021.01); *A61B 5/263* (2021.01); *A61B 5/265* (2021.01); *A61N 1/046* (2013.01); *A61N 1/0492* (2013.01)

(58) Field of Classification Search
None
See application file for complete search history.

(56) References Cited

U.S. PATENT DOCUMENTS 4,787,390 A * 11/1988 Takata ............... A61N 1/04
600/397
5,080,099 A     1/1992 Way et al.
(Continued)

FOREIGN PATENT DOCUMENTS

WO    2002/098502        12/2002
WO    2011076886 A2      6/2011
(Continued)

OTHER PUBLICATIONS

International Search Report Form PCT/ISA/220, International Application No. PCT/US2019/048452, pp. 1-10, dated Oct. 31, 2019.
(Continued)

*Primary Examiner* — John R Downey
*Assistant Examiner* — Anant A Gupta
(74) *Attorney, Agent, or Firm* — Bond, Schoeneck & King, PLLC; Frederick J. M. Price

(57) ABSTRACT

An electrode pad with a defibrillation circuit and a separate ECG tracing circuit. The electrode pad includes a foam base layer, first and second conductive layers, and a hydrogel layer. The foam base layer has a first side and the first conductive layer is centrally located on the base layer. The first conductive layer has a first circuit configured to provide a defibrillation current. The second conductive layer extends at least partially around the first conductive layer on the first side of the base layer. The second conductive layer has a separate second circuit configured to receive an electrical signal. The hydrogel layer covers the first and second conductive layers on the first side of the base layer. The electrode pad additionally includes an electrical connector attached to the first and second conductive layers. The electrical connector is configured for providing a voltage to the first and second conductive layers.

13 Claims, 1 Drawing Sheet

(51) Int. Cl.
    *A61B 5/265*     (2021.01)
    *A61B 5/33*     (2021.01)
    *A61N 1/00*     (2006.01)
    *A61N 1/04*     (2006.01)

(56) References Cited

U.S. PATENT DOCUMENTS

| | | |
|---|---|---|
| 7,277,751 B2 | 10/2007 | Dupelle et al. |
| 2006/0074452 A1* | 4/2006 | Dupelle ............... A61N 1/3702 |
| | | 607/142 |
| 2007/0088419 A1 | 4/2007 | Fiorina et al. |
| 2010/0331659 A1 | 12/2010 | Sheraton, Sr. et al. |
| 2013/0060098 A1* | 3/2013 | Thomsen ............ A61B 5/0816 |
| | | 600/479 |
| 2015/0173639 A1* | 6/2015 | Ichida ................ A61N 1/0472 |
| | | 600/397 |
| 2018/0250159 A1* | 9/2018 | DeSeve, III ............ A61F 7/007 |
| 2019/0046065 A1* | 2/2019 | Macur .................... A61N 1/046 |

FOREIGN PATENT DOCUMENTS

| | | | |
|---|---|---|---|
| WO | 2014007307 | 1/2014 | |
| WO | 2017035502 | 3/2017 | |
| WO | WO-2019241753 A1 * | 12/2019 | ........... A61B 5/0002 |

OTHER PUBLICATIONS

JP Office Action, App. No. 2021-510176, dated Apr. 5, 2022, pp. 1-8.

\* cited by examiner

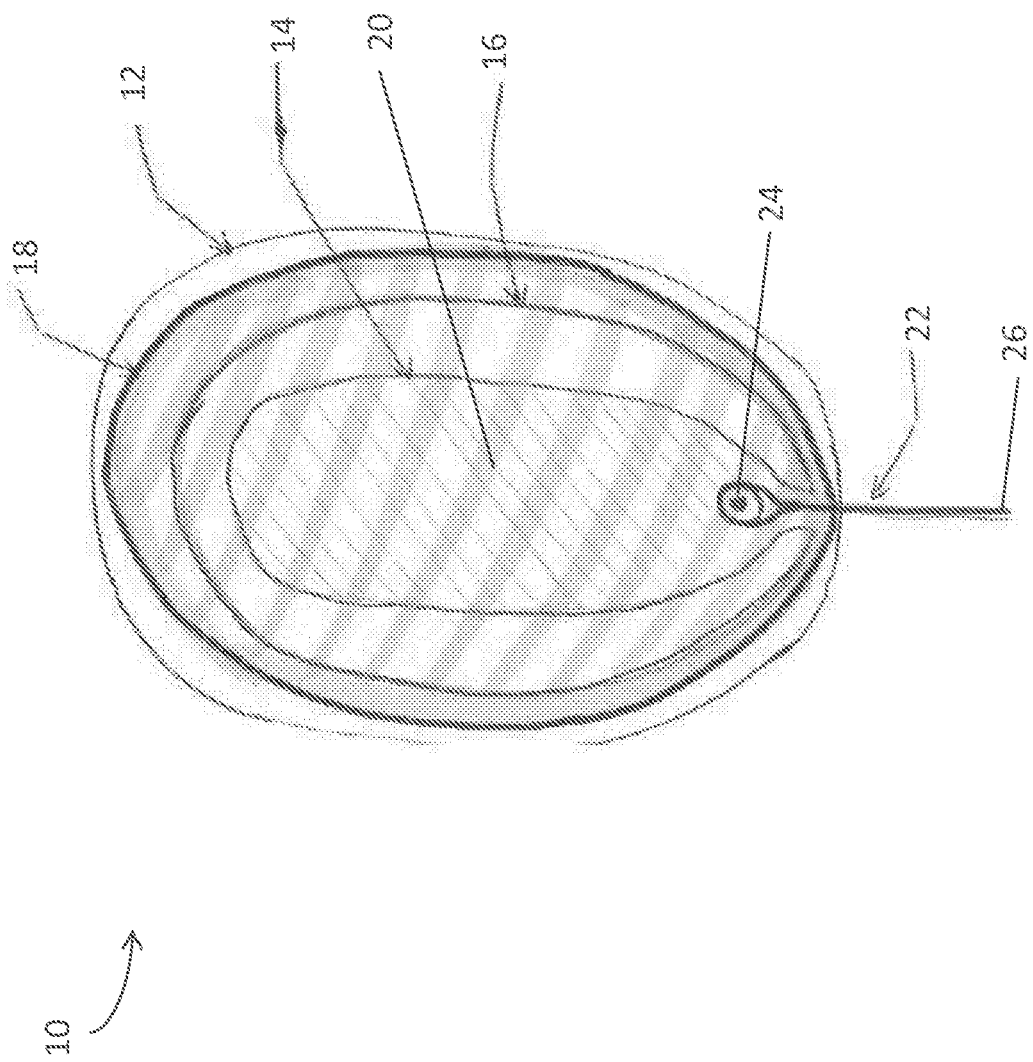

SEPARATE PRINTED TRACES FOR ECG AND DEFIBRILLATION CIRCUITS

CROSS-REFERENCES TO RELATED APPLICATIONS

This application is a national stage application under 35 U.S.C. 371 based on international patent application PCT/US19/48452 filed on Aug. 28, 2019, which claims priority to U.S. Provisional Patent Application Ser. No. 62/725,311, filed on Aug. 31, 2018, and entitled "Separate Printed Traces for ECG and Defibrillation Circuits," the entirety of which is incorporated herein by reference.

BACKGROUND OF THE INVENTION

1. Field of the Invention

The present invention is directed generally to a medical device and, more particularly, to an electrode pad with a defibrillation circuit and a separate ECG tracing circuit, each composed of conductive ink.

2. Description of Related Art

Biomedical electrodes are typically used in electrocardiography and like diagnostic procedures as well as for long term monitoring where a patient must be electrically connected to a test or monitoring device. Such electrodes often consist of three distinct layers: a conductive surface layer of about one square inch, an insulator on one side of the conductive surface layer with graphics imprinted thereon, and a medical gel provided on the other side of the conductive surface layer. The medical gel is used to anchor the electrode to the skin of the patient. The conductive surface layer can be a metallic layer or even conductive ink.

In use, the leadwires of an ECG (or like device) typically include clips or the like at the end thereof which are attached to dedicated connection portions or projections of the electrodes. Such connection portions can be shaped as a mitten (thumb imprint—semi circular) or a fish tail and may be located where the medical gel is absent. Due to the relatively large size (and weight) of the leadwire compared to the electrode, coupled with the inherent tendency of the leadwire to coil, a pulling force is often exerted on the electrode which may peal the electrode from the skin as the medical gel is only a somewhat weak adhesive. There also frequently arises pulling forces as a result of patient movement, both as a result of desired movements and unintended movements. Besides a full pealing off, the force may also only disturb or partially peal the electrode from the skin, resulting in distorted signals (as by noise or artifact) and unusable results. In any event, time and effort are wasted. Further, once an electrode is pealed off, or partially pealed off, it may not be capable of being re-anchored properly so that a new electrode must then be used.

Multifunction Electrode (MFE) pads are a specific type of biomedical electrode that are widely used in the treatment and diagnosis of cardiac ailments. Health care professionals and other first-aid providers use MFE pads to monitor the electrical potential during a heartbeat, to provide high-energy electrical stimulation for defibrillation, and to provide lower level electrical stimulation for pacing. Prior to the development of such pads, care providers were required to apply multiple types of pads and possibly use other means of transferring electric current to the patient (i.e., paddles). As one can easily imagine, the use of multiple electrodes along with the use of other devices leads to potential errors and further injury when implemented during an emergency situation.

The creation of a true MFE pad requires designers to balance many factors, not the least of which is price, since the pads are single-use only. A modern MFE pad must be able to transfer short bursts of significant electrical energy while being able to dissipate such energy quickly so that monitoring remains unaffected. However, in most biomedical electrodes (and MFE pads), the ECG trace and the defibrillation current are part of one electrical circuit. Thus, the ECG trace can be affected by the high voltage and current utilized for defibrillation.

Therefore, there is a need for a biomedical electrode with a separate circuit for the ECG trace and the defibrillation.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a defibrillation pad or electrode with a defibrillation circuit and a separate ECG tracing circuit, each composed of conductive ink. According to one aspect, the present invention is an electrode pad. The electrode pad includes four layers, a base layer, a first conductive layer, a second conductive layer, and a hydrogel layer. The base layer has a first side and the first conductive layer is centrally located on the base layer. The second conductive layer extends at least partially around the first conductive layer on the first side of the base layer. The hydrogel layer covers the first and second conductive layers on the first side of the base layer.

According to another aspect, the electrode pad includes a foam base layer having a first side. The electrode pad also includes a first conductive layer having a first circuit centrally located on the base layer and the first conductive layer is configured to provide a defibrillation current. The electrode pad further includes a second conductive layer having a separate second circuit extending at least partially around the first conductive layer on the base layer. The second conductive layer is configured to receive an electrical signal. The electrode pad additionally includes a hydrogel layer covering the first and second conductive layers on the first side of the base layer.

According to yet another aspect, the electrode pad includes a foam base layer with a first side. The electrode pad also includes a first conductive layer having a first circuit centrally located on the base layer, a second conductive layer having a separate second circuit extending at least partially around the first conductive layer on the base layer, and a hydrogel layer covering the first and second conductive layers on the first side of the base layer. The electrode pad additionally includes an electrical connector attached to the first and second conductive layers. The electrical connector is configured for providing a voltage to the first and second conductive layers.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

FIG. 1 is a first side view schematic representation of an electrode pad, according to an embodiment.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Referring now to the FIGURES, wherein like reference numerals refer to like parts throughout, FIG. 1 shows a first side view schematic representation of a biomedical electrode 10, according to an embodiment. In FIG. 1, the biomedical electrode 10 is a flexible electrode pad (used interchangeably herein with "defibrillation pad"). The electrode pad 10 is configured for providing an electrical connection or path for electrical energy through the electrode pad 10 to a suitable surface, such as the skin surface of a patient. Even though this is the electrical path taken for purposes of clarity to a reader, it should be well understood that electrode pads 10 are bi-directional in terms of electrical energy. For example, an electrode pad 10 that functions as an anode (positive current into a patient) may also function to receive electrical signals from biological sources of energy within the patient.

In the depicted embodiment, the electrode pad 10 is comprised of multiple layers of materials to affect the transfer of electrical energy between an electrical device and the patient. As shown in FIG. 1, the electrode pad 10 generally comprises a base layer 12, a first conductive ("defibrillation") layer 14, a second conductive ("ECG trace") layer 16, and a hydrogel layer 18. The base layer 12 is composed of a foam material. The foam material includes any suitable carrier materials, such as polyethylene. As shown in FIG. 1, the base layer 12 comprises the largest surface area as compared to each of the remaining layers 14, 16, 18 of the electrode pad 10. The base layer 12 of foam is particularly sized to cover the conductive layers 14, 16 and hydrogel layer 18. The added size allows the foam base layer 12 to extend beyond the periphery of the remaining layers 14, 16, 18 to insulate and protect the conductive layers 14, 16 and hydrogel layer 18 while adding additional adhesive capacity around the periphery of the electrode pad 10.

The first conductive layer 14 is a defibrillation layer. Accordingly, the purpose of the first conductive layer 14 is to provide the defibrillation current to the patient. In an embodiment, the first conductive layer 14 is comprised of highly conductive ink 20. The highly conductive ink 20 can be composed of silver chloride or other ink combinations (as should be understood by a person of ordinary skill in the art in conjunction with a review of this disclosure). The highly conductive ink 20 can be applied to or printed on the base layer 12 over the entire surface (i.e., a large surface area) or in a pattern, if desired. In a preferred embodiment, the highly conductive ink 20 is printed on a large surface area of the base layer 12 to optimize the defibrillation energy provided. Printing the first conductive layer 14 directly on to the foam base layer 12 simplifies process steps and decreases additional layers of materials to further simplify the assembly of the electrode pad 10.

As stated above, the electrode pad 10 additionally includes a second conductive layer 16. In the embodiment shown in FIG. 1, the second conductive layer 16 is a separate ECG trace layer. The ECG trace layer 16 is separate from the defibrillation layer 14 so that ECG monitoring of the patient can be achieved while defibrillation current is applied to the patient. In an embodiment, the second conductive layer 16 is comprised of conductive ink. However, according to an embodiment, the second conductive layer 16 is composed of ink that is less conductive than the conductive ink comprising the first conductive layer 14. A purpose of the less conductive ink is that the defibrillation energy will take the path of least resistance (large, highly conductive surface), and not pass through the lesser conductive ECG circuit, therefore decreasing the defibrillation recovery time to obtain ECG trace after defibrillation. The second conductive layer 16 is similarly applied or printed directly on to the foam base layer 12 to simplify process steps and minimize the number of layers of materials comprising the electrode pad 10. The second conductive layer 16 comprises an ionizing surface, such as a chloride surface to assist in quick defibrillation recovery of the hydrogel layer 18, if necessary.

As shown in FIG. 1 and stated above, the electrode pad 10 includes a hydrogel layer 18. In an embodiment, the hydrogel layer 18 is composed of a conductive gel. The conductive gel helps to ensure contact between the conductive layers 14, 16 and the patient's body. The hydrogel functions to wet the patient's skin making it more accepting to the flow of electrical energy. The physical properties of the hydrogel also help to ensure contact over the entire surface of the exposed gel to distribute the energy being transferred. Additionally, the hydrogel layer 18 functions as an adhesive helping to ensure that distributed contact with the patient is maintained. The hydrogel layer 18 can be poured into place on the first and second conductive layers 14, 16 and cured or cast onto the first and second conductive layers 14, 16. The hydrogel layer 18 may have separate properties for a portion that extends over the first conductive layer 14 and a portion that extends over the second conductive layer 16 (defibrillation trace), or the hydrogel may be homogenous throughout the entirety of the hydrogel layer 18.

Still referring to FIG. 1, the electrode pad 10 additionally includes a cord set connector 22. In the depicted embodiment, the cord set connector 22 is connected to the electrode pad 10 and extends outwardly therefrom. At one end 24, the cord set connector 22 is electrically connected toward the center of the first conductive (defibrillation) layer 14. The cord set connector 22 is also connected to the second conductive (ECG trace) layer 16. The other, free end 26 of the cord set connector 22 extends from the electrode pad 10 and is configured to connect to a power (i.e., voltage) source (or other electrical device). Thus, the cord set connector 22 supplies voltage to and from the first and second conductive layers 14, 16.

Having the second conductive (ECG trace) layer 16 separate from the first conductive (defibrillation) layer 14 has two effects on the electrode pad 10. Specifically, if the defibrillation current (from the first conductive layer 14) can be focused to the center of the electrode pad 10 with separate traces (of the second conductive layer 16) branched off for ECG monitoring, then the hydrogel layer 18 over the second conductive (ECG trace) layer 16 will not see high voltage and current. In doing so, the hydrogel layer 18 will not polarize or will have limited polarization over the separate ECG trace (layer 16). When the hydrogel layer 18 polarizes due to high voltage and current, there can be a delay in the ability of the hydrogel layer 18 to transition back to the defibrillator or monitor an ECG trace. Thus, by separating the conductive layers 14, 16, the hydrogel layer 18 over the second conductive (ECG trace) layer 16 will not be subjected to high voltage and current and the delay between defibrillation and re-establishment of ECG tracing is decreased. Additionally, maintaining a separate second conductive layer 16 for ECG tracing allows the electrode pad 18 to provide a clearer ECG trace as the ECG trace is less likely to be affected by the high voltage and current utilized for defibrillation.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. An electrode pad, comprising:
a base layer comprising a first side;
a first conductive layer centrally located on the base layer;
a second conductive layer extending at least partially around the first conductive layer on the base layer; and
a hydrogel layer covering said first and second conductive layers and extending at least partially around an outside of the first conductive layer and an outside of the second conductive layer on said first side of said base layer,
wherein the second conductive layer comprises an ionizing surface for accelerating defibrillation recovery of the hydrogel layer after defibrillation.

2. The electrode pad of claim 1, wherein the first side of the base layer comprises a surface area which is larger than a surface area of each of the first and second conductive layers.

3. The electrode pad of claim 1, wherein the first conductive layer and second conductive layer are composed of conductive ink.

4. The electrode pad of claim 3, wherein the conductive ink of the first conductive layer is more conductive than the conductive ink of the second conductive layer.

5. The electrode pad of claim 3, wherein the conductive ink is printed on the base layer.

6. The electrode pad of claim 1, wherein a first portion of the hydrogel layer extending over the first conductive layer has a first set of properties and a second portion of the hydrogel layer extending over the second conductive layer has a second set of properties which is different from the first set.

7. The electrode pad of claim 1, wherein the base layer is composed of foam material.

8. The electrode pad of claim 1, wherein at least one of the first conductive layer and second conductive layer is composed of silver chloride.

9. An electrode pad, comprising:
a foam base layer comprising a first side;
a first conductive layer comprising a first circuit centrally located on the base layer;
wherein the first conductive layer is configured to provide a defibrillation current;
a second conductive layer comprising a separate second circuit extending at least partially around the first conductive layer on the first side of the base layer;
wherein the second conductive layer is configured to receive an electrical signal;
a hydrogel layer covering the first and second conductive layers and extending at least partially around an outside of the first conductive layer and an outside of the second conductive layer on the first side of the base layer; and
wherein the second conductive layer comprises an ionizing surface for accelerating defibrillation recovery of the hydrogel layer after defibrillation.

10. The electrode pad of claim 9, wherein when a first voltage is provided to the first conductive layer, the first voltage is configured to be separate from a voltage provided to the second conductive layer.

11. An electrode pad, comprising:
a foam base layer comprising a first side;
a first conductive layer comprising a first circuit centrally located on the base layer;
a second conductive layer comprising a separate second circuit extending at least partially around the first conductive layer on the first side of the base layer;
a hydrogel layer covering the first and second conductive layers and extending at least partially around an outside of the first conductive layer and an outside of the second conductive layer on the first side of the base layer; and
an electrical connector attached to the first and second conductive layers configured for providing a voltage to the first and second conductive layers; and
wherein the second conductive layer comprises an ionizing surface for accelerating defibrillation recovery of the hydrogel layer after defibrillation.

12. The electrode pad of claim 11, wherein the electrical connector comprises an end connected to the first and second conductive layers and a free end configured to connect to a voltage source.

13. The electrode pad of claim 1, wherein the first conductive layer comprises a first circuit and the second conductive layer comprises a separate second circuit.

* * * * *